(12) United States Patent
Kristal et al.

(10) Patent No.: US 6,558,955 B1
(45) Date of Patent: May 6, 2003

(54) METHODOLOGY FOR PREDICTING AND/OR DIAGNOSING DISEASE

(75) Inventors: Bruce S. Kristal, White Plains, NY (US); Wayne R. Matson, Ayer, MA (US); Paul E. Milbury, Ipswich, MA (US)

(73) Assignees: Esa Inc., Chelmsford, MA (US); Board of Regents, University of Texas Systems, Austin, TX (US); Cornell Research Foundation, Inc., Ithaca, NY (US)

( * ) Notice: Subject to any disclaimer, the term of this patent is extended or adjusted under 35 U.S.C. 154(b) by 0 days.

(21) Appl. No.: 09/424,805

(22) PCT Filed: Mar. 29, 1999

(86) PCT No.: PCT/US99/06762

§ 371 (c)(1),
(2), (4) Date: Feb. 8, 2000

(87) PCT Pub. No.: WO99/50437

PCT Pub. Date: Oct. 7, 1999

Related U.S. Application Data

(60) Provisional application No. 60/079,935, filed on Mar. 30, 1998, now abandoned.

(51) Int. Cl.[7] ............... G01N 33/48; C12Q 1/00; C12M 1/00; C12M 1/36; C12M 1/34
(52) U.S. Cl. ............... 436/63; 436/64; 435/4; 435/283.1; 435/287.1; 435/288.6; 435/803
(58) Field of Search ............... 435/4, 283.1, 280, 435/287.1, 803, 288.6; 436/63, 64

(56) References Cited

U.S. PATENT DOCUMENTS

| | | | |
|---|---|---|---|
| 3,855,099 A | 12/1974 | Matson | 204/195 |
| 4,263,268 A | 4/1981 | Knox et al. | 423/449 |
| 4,404,065 A | 9/1983 | Matson | 204/1 |
| 4,413,505 A | 11/1983 | Matson | 73/61 |
| 4,500,432 A | 2/1985 | Poole et al. | 210/659 |
| 4,552,013 A | 11/1985 | Matson | 73/61 |
| 4,804,455 A | 2/1989 | Matson | 204/411 |
| 4,812,344 A | 3/1989 | Jaeger et al. | 428/34.6 |
| 4,863,873 A | * 9/1989 | Matson | |
| 4,976,994 A | 12/1990 | Matson | 427/230 |
| 5,011,608 A | 4/1991 | Damjanovic | 210/656 |
| 5,032,240 A | 7/1991 | Argade | 204/132 |
| 5,063,064 A | 11/1991 | Bourbon et al. | 424/673 |
| 5,098,576 A | 3/1992 | Cabrera et al. | 423/656 |
| 5,252,333 A | 10/1993 | Horrobin | 424/422 |
| 5,358,802 A | 10/1994 | Mayer et al. | 429/218 |

FOREIGN PATENT DOCUMENTS

| | | | |
|---|---|---|---|
| EP | 0042683 | 12/1981 | G01N/1/22 |
| EP | 0365327 | 4/1990 | C04B/38/00 |

OTHER PUBLICATIONS

Verdery et al., Am.J.Physiol. Oct. 1997, v273, pp. E714–E719.*

Tockman et al. (Cancer Res., 1992, 52:2711s–2718s.*

Marz et al., (Clin Chem. 1993, vol. 11 Part 1, pp. 2276–2281).*

Webster's Ninth New Collegiate Dictionary, Merriam Webster Inc., Springfield, MA (1987), p 227.

Shinenaga et al, "In Vivo Oxidatibe DNA Damage: Measurement of . . . ", Methods of Enzymology, vol. 186, (1990), pp 521–530.

Teixeira et al, "Analysis of 8–Hydroxy–2'–deoxyguanosine in Rat urine and Liver DNA . . . ", Analytical Biochemistry, vol. 226, pp. 307–319, (1995).

Pilger et al, "Assay for the determination of urinary 8–hydroxy–2'–deoxyguanosine by high–performance liquid chromatography with electrochemical detection", Journal of Chromatography B, vol. 689, (1997) pp 399–403.

Inamoto et al, "Liquid chromatography of guanidino compounds using a porous graphite carbon column and application to their analysis in serum", Journal of Chromatography B, 707 (1998) pp 111–120.

Berek et al, "Use of porous pyrolytic carbon for analytical and microscale high–performance liquid chromatographic bioseparations", Journal of Chromatography B, 718 (1998) pp 187–192.

Xie et al, "Determination of an Oxidation Product of Guanine in DNA . . . ", Current Separations, 13:1, pp 18–21, (1994).

Chemical Abstract, DN 98:175747, Stulik et al,J. Chromatogr, 273(1), pp 77–86 (abstract only).

Database MEDLINE, AN 91248001, Granzotti et al,Nutrional Index in heart disease in childhood. Dec. 1990, vol. 55, No. 6, pp 371–373 (Abstract only).

Database MEDLINE, AN 91108912, Abad–Lacruz et al,Parental and Enteral Nutrition, Nov.–Dec. 1990, vol. 14, No. 6, pp 618–621 (Abstract only).

* cited by examiner

*Primary Examiner*—Anthony C. Caputa
*Assistant Examiner*—Gary B. Nickol
(74) *Attorney, Agent, or Firm*—Hayes Soloway P.C.

(57) ABSTRACT

Disorders are diagnosed by analyzing biological samples of ad libitum-fed and dietary-restricted individuals to generate frequency distribution patterns representative of molecular constituents of the samples, and comparing the patterns.

18 Claims, 6 Drawing Sheets

α-methythistidine
1-methylhistidine
2-hydroxyphenylacetic acid
3,4-dihydroxymandelic acid
3,3,5-triiodothyronine
3,4-dihydroxyphenylacetic acid
3,0-methyldopa
3-hydroxy-4-methylphenethylamine
3-hydroxyanthranilic acid
3-hydroxykynurenine
3-hydroxymandelic acid
3-hydroxyphenylacetic acid
3-methoxy-4-hydroxyphenylglycol
3-methoxytyramine
3-methylhistidine
4-hydroxy-3-methylmandellic acid
4-hydroxybenzoic acid
4-hydrocyphenylacetate
4-hydrocyphenylacetate
4-O-methyldopamine
5-hydroxyindoleacetic acid
5-hydroxytrptophan
5-hydroxytryptophol
5-methoxytryptamine
5-methoxytryptophan
5-methoxytryptophol
5-methylcysteine
6-hydroxymelatonin
7-methylguaninne
7-methylxanthine
acetylhistidine
anserine
anthranillic acid
ascorbic acid
carnosine
cysteine
dopamine
epinephrine ferulic acid
glutathione
glutathione disulfide
guanine
homocarnosine
homogentisec acid
homovanillic acid
homovanyllyl alchohol
homoveratic acid
hypoxanthine
indole-3-lactic acid
indole-3-propionic acid
indoleacetic acid
isatin
isoproterenol
kynurenine
levodopa
melatonin
metanephrine
methionine
methoxamine
n-acetylserotonin
n-methylserotonin
norepinephrine
normetanephrine
pyridoxal
serotonin
tryptamine
tryptophan
tryptophol
tyramine
tyrosine
uric acid
vanillic acid
vanillylmandelic acid
xanthine
xanthosine

FIG. 3

|  | Retention Time | Array Channel | Aprox. Oxidation Potential | |
|---|---|---|---|---|
| Compound 52 | 26.37 | 10 | 530 | |
| Compound 55 | 27.98 | 9 | 460 | |
| Compound 69 | 35.08 | 16 | 950 | or higher |
| Compound 87 | 46.83 | 16 | 950 | or higher |
| Compound 89 | 49.72 | 8 | 390 | |
| Compound 93 | 51.92 | 8 | 390 | |
| Compound 114 | 59.81 | 16 | 950 | or higher |
| Compound 117 | 62.16 | 7 | 320 | |
| Compound 123 | 63.30 | 16 | 950 | or higher |
| Compound 132 | 67.24 | 14 | 810 | |
| Compound 139 | 69.78 | 11 | 600 | |
| Compound 147 | 72.18 | 8 | 390 | |
| Compound 173 | 81.82 | 9 | 460 | |
| Compound 174 | 83.88 | 6 | 250 | |
| Compound 180 | 88.61 | 13 | 740 | |
| Compound 181 | 88.57 | 10 | 530 | |
| Compound 188 | 92.24 | 10 | 530 | |
| Compound 189 | 92.43 | 9 | 460 | |
| Compound 191 | 93.79 | 5 | 180 | |
| Compound 203 | 96.99 | 8 | 390 | |
| Compound 209 | 98.53 | 6 | 250 | |
| Compound 215 | 101.64 | 10 | 530 | |

FIG. 6

METHODOLOGY FOR PREDICTING AND/OR DIAGNOSING DISEASE

This application claims benefit to U.S. Provisional Application No. 60/079,935, filed Mar. 30, 1998, now abandoned.

The U.S. Government has a paid-up license in this invention and the right in limited circumstances to require the patent owner to license others on reasonable terms as provided for by the terms of Grant Nos. AG01188 and AG15354 awarded by The National Institute of Health Department of Health and Human Services.

FIELD OF THE INVENTION

This invention in one aspect relates to a method for predicting and/or diagnosing diseases in living animals. The invention has particular utility in diagnosing and/or predicting future risk of specific diseases in living animals and will be described in connection with such utility, although other utilities are contemplated. This invention in another aspect relates to identification of markers for diseases or subclinical conditions that in the future may develop into diseases that are capable of distinguishing groups, and to subsets of these markers, where the utility of such markers can, for example, be determined by univariate, multivariate, or pattern recognition based analyses, and/or where the markers identified as important by the approach described also can be measured using other analytic approaches. The invention has particular applicability to predicting risk to cancer, type II diabetes, cardiovascular disease, cerebrovascular disease, and other diseases whose etiology has been established to or hypothesized to be modulated by diet or nutrition, i.e. neurogenerative disorders such as Alzheimer's Disease, Parkinson's Disease and Huntington's Disease {1}, and will be described specifically in connection its utility for using serum or plasma metabolites for determining breast cancer risk; however, other utilities and other tissue or biological fluid samples (e.g., whole blood, cerebrospinal fluid, urine, and/or tissue samples) may be used instead of blood, and diseases and conditions other than breast cancer also can be addressed, as noted above. Similarly, in addition to disease, the assessment of nutritive status (over long or short term), may be utilized in accordance with yet another aspect of the present invention as a medical test under a variety of potential clinical settings, or in controlling epidemiological or pharmaceutical testing. Still other utilities, e.g. for detecting exposure to and/or sensitivity to exposure to toxins, are contemplated.

BACKGROUND OF THE INVENTION

Dietary restriction (DR), i.e. underfeeding without malnutrition, has established efficacy in reducing both degenerative and neoplastic diseases. DR has been extensively explored since its first use in the 1930's because of its ability to extend both mean and maximum life span, reduce age-related morbidity, and delay or prevent certain age-associated physiological dysfunction {2, 3}. DR also alters many basic physiological processes, including metabolism, hormonal balance, and the generation of, detoxification of, and resistance to reactive oxygen species {4}. DR can be implemented in multiple ways {e.g. 5–13}. Moreover, restriction of total calories is believed to be more important than reducing intake of specific factors (e.g. fat, proteins, vitamins and minerals, etc. {14, 15}). DR reportedly extends longevity in essentially all animals in which it has been tried, including multiple mammalian species (rat, mouse, guinea pig {2, 5–13, 16}). Furthermore, promising data suggest that at least some of the benefits of DR, especially those regarding glucose metabolism, also occur in non-human primates {17–21}, and perhaps, in humans as well {22,23}. Together, these observations suggest that the DR effect is robust in mammals.

DR has been shown to reduce both incidence and severity of non-neoplastic diseases. One example is the efficacy of DR against glomerulonephritis, periarteritis, and myocardial degeneration in both male and female Sprague-Dawley rats. Similar observations have been made in other strains and other diseases, such as lung disease {25}. DR is also effective at preventing some strain specific disease, such as auto-immune disease in NZB/NZWF1 mice {26} and in MRL/1pr mice {27}, and atherosclerotic {28} and myocardial ischemia lesions in JCR:LA-cp mice {29}.

DR also has been shown to reduce both incidence and severity of neoplastic diseases. DR-mediated reduction of neoplasia includes delayed onset of leukemia, pituitary adenomas, mammary and prostatic tumors, and hepatomas {30, 31}. Observations of the effects of DR on mammary tumors {32–36} are typical. DR acts to reduce breast cancer both by delaying onset (both by reducing initiation events and slowing promotion) and by slowing tumor progression {30}. In transgenic mice prone to mammary tumors, DR reduced tumor incidence by 67% {32}. This result reveals that DR is capable of overcoming genetic predisposition to breast cancer. Studies {33} in rats treated with a carcinogen demonstrated that high fat and high calorie diets are co-carcinogenic, and that none of the rats maintained on 40% DR regimen developed mammary tumors, while 60% of AL-fed rats did. Concerns that this effect may have been partially mediated by reducing fat availability for tumor growth led to later studies {34}. Despite a higher fat content in the DR diet, results show a 75% reduction in rats with mammary tumors and in the number of tumors per animal in the tumor-bearing group. Even more impressively, DR reduced total tumor yield, average tumor size, and mean tumor burden by 93–98%. Notably, Sinha et al demonstrated that even a 20% DR regimen reduces tumors by 65%, without effects on hormone levels or fertility {35}.

Thus, DR mediated protection against breast cancer in laboratory models is: 1) substantial (as much as 100% reduction in cancer rates {32}) and highly replicable {30–34}; 2) robust and well-documented in a variety of animal models, including a model of genetic predisposition and a model of carcinogen exposure {31, 32}; 3) seen even with a more moderate (20%) restriction paradigm that does not affect fertility or hormone levels {34}; 4) effective at multiple levels (initiation, promotion, progression). Thus, the present invention, in one aspect, is based on the observation that different subsets of markers that reflect DR are predictive for different diseases. For example, identifying markers, for example in sera, that reflect the DR phenotype, would lead to markers that would reflect risk of developing breast cancer, or other conditions affected by diet.

Consistent with its broad effects on longevity and disease, DR is a systemic phenomenon, and its effects include measurable differences in blood constituents relative to those seen in ad libitum fed (AL) animals {37}. Many previous studies have focused on measurement of hormones. For instance, studies have shown alterations in plasma corticosterone patterns and levels {38}; some female reproductive hormones {39}, plasma chlecystokinin decreases 50% {40}; T3 but not T4 is reduced {41}; and plasma insulin drops as much as 60% in some DR models {42}. While informative, these studies have been somewhat limited by the technical complexity involved (e.g. circadian cyclicity, rapid response to stimuli). Other studies seeking more stable markers have examined markers of energy and free radical metabolism, revealing that DR decreases plasma glucose, ascorbate (e.g. 43–45) and glycohemoglobin levels {43}. Overall, the data indicates that differences in serotype distinguish AL and DR animals, and that these differences include some metabolites that are both relatively easy to assay and which reflect the beneficial effects of DR on physiology, metabolism and free radical biology (e.g. generation, sensitivity, and detoxification).

While not wishing to be bound by theory, since the AL and DR serotypes reflect robust physiological differences between these groups, it is believed that these serotypes include metabolites or metabolite profiles that cross-species and predict relative risk for the development of disease in humans. Data consistent with this concept comes from studies showing that the effect of DR on breast cancer is largely driven by chronic effects (termed promotion) rather than acute effects (termed initiation {30, 31}). These data would imply that relative risk of developing breast cancer is likely reflected in general metabolism over long periods of time. Relative risk should thus be detectable in sera long before the development of overt disease. In the case of humans, who lie on a broad spectrum with respect to caloric intake, it is believed that closer fit to the AL serotype (i.e. the biological response typical of a high caloric intake) would predict higher relative risk of disease, whereas greater fit to the DR serotype (i.e. the biological response typical of a lower caloric intake) would be associated with reduced risk. While previous studies demonstrated differences between AL and DR animals, they were believed only able to look at specific, predetermined markers, making it essentially impossible to conduct a sufficiently broad and powerful search to identify markers of use for determining nutritional status or predicting health across species.

SUMMARY OF THE INVENTION

The present invention provides a system, i.e. method and apparatus, for determining differences in concentrations of molecules, in particular small molecule metabolites, between animals whereby to create a metabolite database which may be used to reproducibly distinguish between two or more states of the health or the nutritive status of an animal. More particularly, the present invention employs analysis techniques to provide a small molecule inventory for metabolic pathway patterns of samples of ad libitum fed (AL) and dietary restricted (DR) individuals whereby to reproducibly distinguish between different dietary status of animals, between health conditions of animals, and to reproducibly predict relative risk for the development of a particular disease in animals.

The basis for this approach is that sufficient specific, reproducible, measurable changes exist in the overall biochemistry of small molecule metabolites among the different states to reproducibly distinguish the two (or more) states of interest. Different entities and/or sub-sets or combinations of markers can be used to identify different diseases or subclinical conditions. An HPLC-electrochemical analysis based approach in accordance with U.S. Pat. No. 4,863,873, which is incorporated herein by reference, has facilitated creation of a database for the constituents of AL and DR serum.

DESCRIPTION OF THE DRAWINGS

For a fuller understanding of the nature and objects of the present invention, reference should be had to the following detailed description taken in conjunction with the accompanying drawings wherein:

FIG. 3 is a table of biochemically identified serum metabolites in accordance with the present invention;

FIG. 6 is a table of biochemically identified subsets of serum metabolites in accordance with the present invention.

DETAILED DESCRIPTION OF PREFERRED EMBODIMENT

Methodology for Sample Analysis and Database Creation

Sample Preparation:

Blood was collected from male Fischer 344 rats by terminal exsanguination following decapitation in accordance with standard animal usage guidelines. Samples were placed on ice for 30 minutes, centrifuged, and the resulting sera snap frozen in liquid nitrogen and stored at minus (−) 80° C. until analysis.

Samples were precipitated and extracted in four vol of acetonitrile(An)/0.4% acetic acid(HAc) at −20° C. One ml of centrifuged supernatant was removed, evaporated to dryness under vacuum, and reconstituted in 200 ml of a Mobile Phase A as described below. This protocol conserves reactive species such as ascorbate, and homogentistic acid at 1 ng/ml concentrations. 100 ml reconstituted extract was placed in each of two auto sampler vials, one immediately analyzed and the other frozen at −80° C. for future confirmation analysis. Prior to injection, samples were maintained at 4° C.

Mobile Phases: Chromatographic solvents include isopropyl alcohol, methanol, acetonitrile, lithium hydroxide, glacial acetic acid, and pentane sulfonic acid. To retain stability of retention times and response potentials, a novel mobile phase pair was developed: Mobile Phase A (11 g/l of PSA at pH 3.00 with acetic acid) and Mobile Phase B (0.1M LiAc at pH 3.00 with acetic acid in 80/10/10 methanol/An/isopropanol). PSA demonstrates an improved ability to solubilize and remove protein and peptide fragments from both HPLC (C18) columns and coulometric detectors while the high organic modifier (Mobile Phase B) effectively removes residual lipids and polysaccharides. Sulfonic acids are, however, inherently contaminated necessitating a cleaning protocol in which the PSA/HAc concentrated buffer (41 of 400 g/l PSA) was electrolyzed over pyrolytic graphite at a potential of 1000 mV vs Pd(H).

Figure 1:
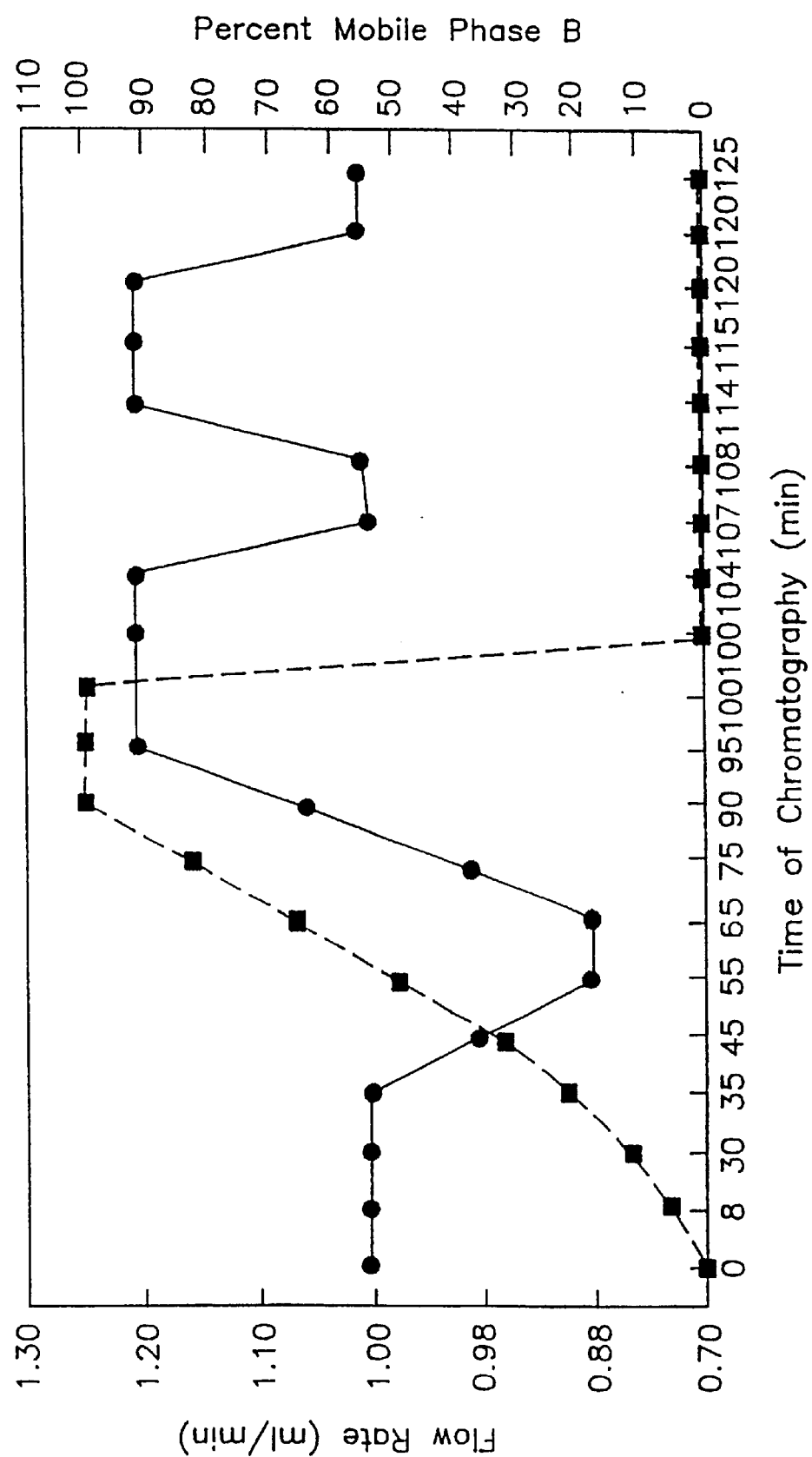
FIG. 1 is a chromatographic method pump profile in accordance with the present invention.

Chromatographic Methods: Referring to FIG. 1, the chromatographic method involves a 120 min complex gradient from 0% Mobile Phase B to 100% Mobile Phase B, with flow rate adjusted to compensate for aziotropic viscosity effects. Gradient operation was provided by two Schimadzu LC-10AD HPLC pumps. Despite meticulous precleaning protocols, and the use of highly purified solvents and selected organic modifiers, spurious peaks occur late in the gradient. This problem was addressed by developing a device based on electrochemically activated porous carbon with sorption characteristics similar to C18. A prototype peak suppresser/gradient mixer (PS/GM) was placed in stream before the HPLC injector. The PS/GM mixer incorporated a 2 cm length of a 1 cm diameter C18 precolumn integral with a 2.5 cm section of rod with flow interrupting grooves that serve to trap and spread mobile phase contaminants. When these were released to the grooved section, during the gradient run, they were mixed to a peak width at a half height of ca. 140 sec. This effectively reduced a mobile phase derived contaminant signal to a wave that was later eliminated during data reduction. The mixed gradient was delivered from the PS/GM to a PEEK lined pulse damper prior to flowing through the auto sampler injector and on to the C18 columns. Sample extracts were separated on dual PTFE lined HR80 columns containing 3-mm ODS particles and measuring 80 mm×4.6 mm I.D.

Analyte detection was accomplished with a NCA Chemical Analyzer, Model CEAS multiple electrode electrochemical detection system, available from ESA, Inc., of Chelmsford, Mass. The latter includes an ESA Model 6210 analytical cell and a 16-channel coulometric electrode array incremented from −100 mV to +940 mV to detect both reducible and oxidizable compounds. PS/GM, pulse damper, columns, and detectors are contained within a temperature controlled enclosure maintained at 35° C. System functions were controlled by the ESA, Inc. Model 4.12 CCEAS software installed on a 386 microcomputer networked to remote 486-based computers where data storage, reduction and analysis were accomplished. CEAS analysis software-produced reports were imported to spreadsheet/database software for further statistical analysis and reports.

Data Reduction, Observation and Analysis: Chromatographic retention times, monitored by pure standards and identified sample compounds, do not vary more than 1%. The absolute qualitative channel ratio responses do not vary by more than 20% and were controlled for by inclusion of authentic standards to within 5%. Where possible, sample chromatographic peak identities were confirmed by spiking with the relevant authentic standard. Final confirmation was made by comparison of the matching ratio (R) of the standard and the sample peaks. R represents the ratio between the dominant oxidation channel and juxtaposition subdominant channels. A given compound is oxidized at a specific potential and therefore any compound can be described by a retention time and a potential. In practice, compounds were oxidized on a dominant detector set near its oxidation potential and exhibited a smaller response on the prior and following detector. The ratio exhibited between the dominant and adjacent detector responses was characteristic of a given compound and variations from that ratio, when a standard was close in concentration to a sample compound, indicated a co-eluting contaminant.

Data from each detector analog signal was converted and combined with other detector data to construct a time-potential map, which was compared with standards and between samples. Analytical values were calculated for sample peaks based on matches under restrictions for retention time, detector channel ratios and, to a lesser degree, peak heights, according to priority optimized by the analyst over sequential monitored analysis. Where compound identity is known, final results were calculated as ng per ml of sample based on standard responses.

To automate analysis, a compound table was generated from a pool of multiple samples in a cohort with concentrations defined as 100. Subsequent sample analysis generates reported values as percentage of pool values. This table was used to analyze (initially with manual oversight, then automatically) all other pools and a few samples within the study. The CEAS analytical software has a built in "learning" capacity, which is inherently part of the "standards" definition function of the analysis. As the operator oversaw a few analyses, decisions were made about parameters such as referencing retention times to other compounds or what degree of variation from the channel ratio's will be tolerated. Conflicts and ambiguity in analysis were monitored and resolved during this test phase of the analysis. Eventually, the pool standard table will "learn" how reliably to find a majority of the potential analytes in the samples. Typically >400 compounds were resolved in plasma at the 20 nanoampere gain. Reported values were captured in a file suitable for downloading into a database.

EXAMPLE 1

Figure 2A:
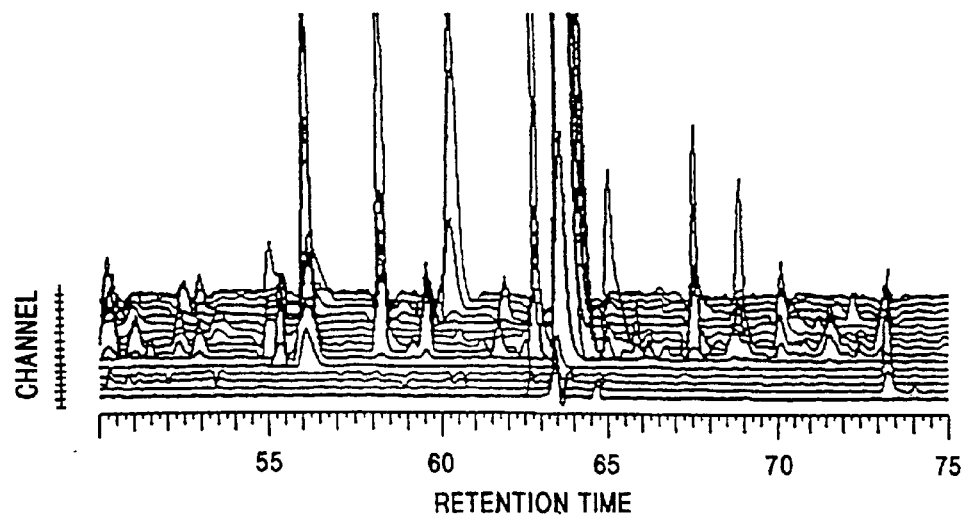
FIGS. 2A–2C are array chromatographs of serum samples in accordance with the present invention.

The use of complex HPLC separations, coupled with coulometric array detectors, enables simultaneous quantitation of >400 compounds from serum (FIG. 2A). The combination of retention time (FIG. 2B) and ratio of response across adjacent detectors (FIG. 2C) in the array enables reproducible identification of a given peak in multiple runs and comparison of samples of interest such as sera from AL and DR rats. In all, ~70 biochemically identified compounds and 350+ currently unidentified compounds were reproducibly measured using these techniques. See Table I, FIG. 3.

HPLC Separations Coupled with Coulometric Array Detection

Figure 2B:
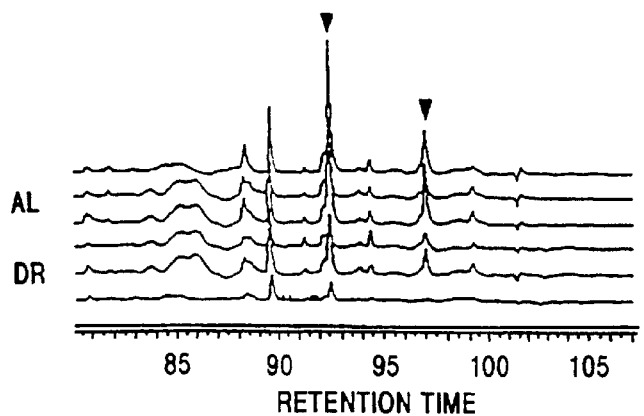
Figure 2C:
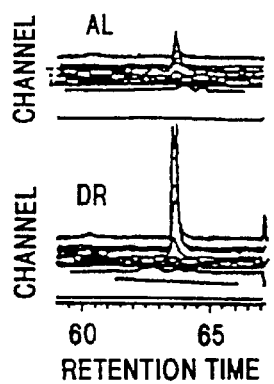

Data was initially generated by CEAS/Coularray systems in the form of a set of 16 chromatograms (one for each detector). FIG. 2A shows approximately one-fifth of a total chromatogram, including ~70 independent, identifiable and quantifiable peaks, from a 6-month old male Fischer 344 rat. Sensor potentials ranged from T, −100 mv to $T_{16}$+940 mv. Results were shown at an intermediate gain (200 nA). The x axis is retention time, y-axis is the magnitude of the response, the 16 parallel traces represent the 16 detectors of the array from 1–16 (bottom to top). FIG. 2B shows a later section of the chromatogram from 3 AL rats (top three traces) and 3 DR rats (bottom three traces). For clarity, only data from channel (detector) 8 is shown (gain=500 nA). Arrows indicate two metabolites that are decreased by DR. FIG. 2C shows the region of the chromatogram from FIG. 2A (compound 123, see FIG. 4) from one AL (top) and one DR (bottom) animal (gain 15 $\mu$A). As in FIG. 2A, the 16 parallel traces represent the 16 detectors of the array from 1–16 (bottom to top). Note that the ratio of response across the detectors is constant.

Figure 4:
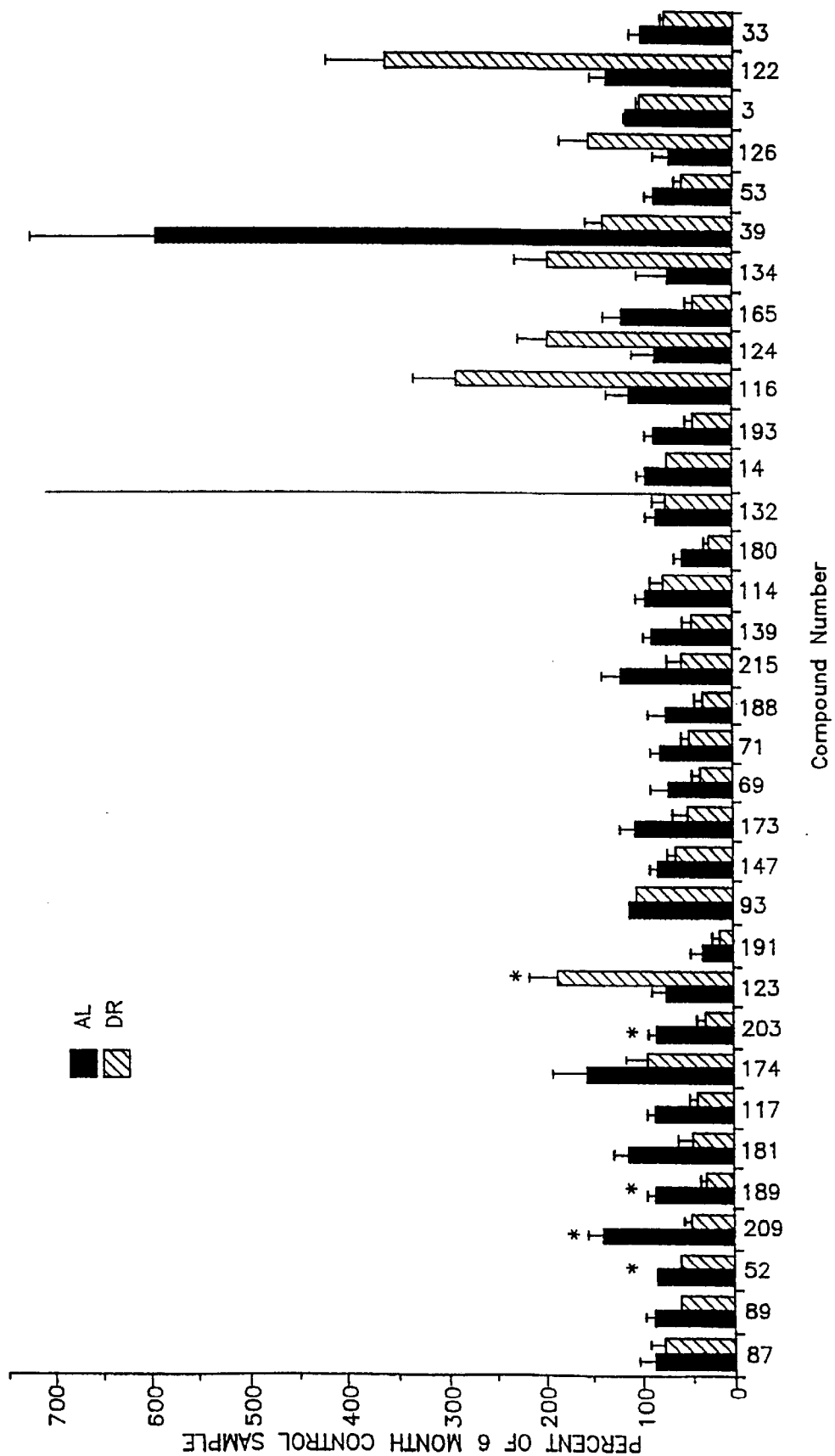
FIG. 4 is a bar graph of biochemically differentiated serum metabolites in accordance with the present invention.
Figure 5A:
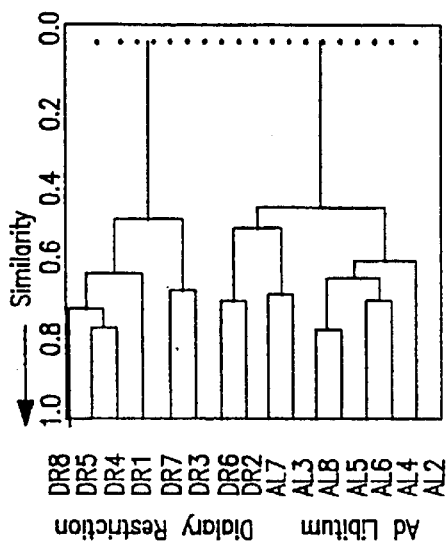
FIGS. 5A and 5B are dendograms and FIGS. 5C and 5D are PCA patterns of biochemically differentiated serum metabolites in accordance with the present invention.
Figure 5B:
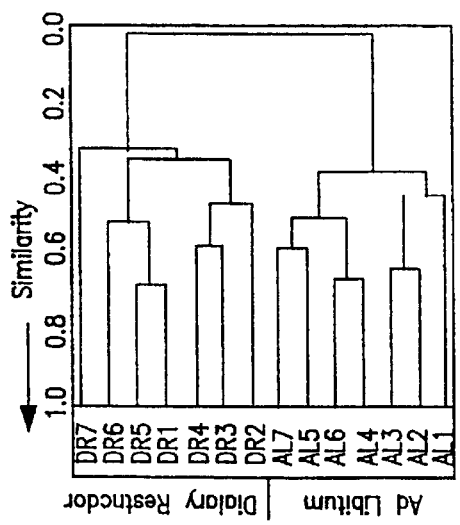

Application of this technology to the study of sera from AL and DR rats has revealed 34 compounds that differ between these groups (FIG. 4). Of these 34 compounds, 6 are reproducibly altered in both 6 and 12 month rats, and at least five of these six are also altered in 18 month rats. The remaining 28 markers include some with apparent age-specificity and others whose validity is still under investigation. These markers, which were originally identified in 6-month old AL and DR rats, differ sufficiently between AL and DR groups to separate animals into the correct dietary group by both hierarchical cluster analysis and principal component analysis (FIG. 5A and 5B).

To verify feasibility, the HPLC system described above was used to determine the relative levels of 217 metabolites from the sera of 6 month old male AL and DR Fischer 344 rats. Analysis revealed 22 metabolites that differed between AL and DR rats by t-test without consideration for the Bonferroni correction (See FIG. 4). These 22 compounds (see Table II, FIG. 6) became the primary variables of interest in a follow-up study (N=8/group, 12 month AL and DR Fischer 344 rats). Analysis of these data confirmed statistical significance of 6 of these 22 compounds (marked by asterisks in FIG. 4). Furthermore, five of these six also statistically differ between 18 month old AL and DR rats (p values <0.02, <0.002, <0.001, <0.0002, <0.0001); the sixth (metabolite #71 which was determined to be homovanillic acid) showed a similar trend, but p>0.05 ($\beta$<0.1, suggesting increasing "N" likely will yield statistical significance). The remaining 16 compounds, as well as 12 compounds that were statistically significant only in the 12 month samples, likely included some that are type I statistical errors, some that may be statistically significant when "N" is increased ($\beta$ currently <0.8 for many, some of which approach statistical significance in the second age group), and some metabolites may only reflect the DR phenotype at specific ages. Further experiments using the methods described can be used to distinguish between these possibilities, and also to identify other markers of interest. Also, another compound was found to decrease >99% following short term caloric restriction.

As will be seen from the foregoing Example, alteration of the dietary paradigm on which animals are maintained can be used to develop specialized patterns or profiles. As examples, tests of male and female rats of different ages enable identification of age- and sex-dependent and -independent profiles associated with DR. Specific changes in the duration and extent of DR feeding regimens enable generation of an extended metabolic database relating markers to long- and short-term caloric intake and balance.

Similarly, the resulting data can be analyzed using univariate statistics (e.g., t-tests), multivariate statistics (e.g., ANOVA) or other multivariate analysis (hierarchical cluster analysis, principal component analysis) or through the use of pattern recognition algorithms to qualitatively and quantitatively identify metabolic profiles and relationships.

Serum Markers for DR

Referring to FIG. 4, sera samples from male Fischer 344 rats were run on an ESA Model CEAS as described above. Sera from 6-month old and 12 month old AL and DR rats were analyzed (N=8/group). Data was expressed as the percentage of the level of analyte present in the sera of one of the 6-month old AL rats. Bars to the left of the vertical line represent compounds that differ statistically between 6 month old AL and DR rats; those bars to the right represent compounds that differ statistically between 12 month old AL and DR rats. Asterisks mark the 6 compounds that differ statistically in both groups (bars show only 6 month data; p values below are the value at 6 months). Out of 217 analytes quantified to date, 34 show p values <0.05 prior to Bonferroni corrections, (uncorrected p values, in order {left of line} p≦0.0008, 0.0008, 0.001, 0.001, 0.005, 0.0073, 0.0089, 0.0091, 0.012, 0.012, 0.013, 0.014, 0.017, 0.017, 0.017, 0.019, 0.023, 0.026, 0.026, 0.037, 0.04, 0.05; {right of line} p≦0.0017, 0.0027, 0.003, 0.0075, 0.011, 0.014, 0.014, 0.016, 0.023, 0.034, 0.035,0.04).

Observations:

The data in FIGS. 2 and 4 show that it is possible to identify metabolic differences in known groups; FIG. 5 shows the reciprocal—that the metabolic profiles generated by coulometric array technology include sufficient information to identify the group to which a sample belongs. Thus, metabolic profiles reflective of long term DR may be used to group human samples, and the groups generated may in turn reflect the samples' identity (e.g., women who later developed breast cancer vs women who remained cancer free), and persons at high risk for development of disease vs persons at low risk for development of disease).

There are five components linking the methodology of the present invention to its utility. The first is the ability to identify an animal system in which disease frequency is reproducibly reduced. This is accomplished by using the dietary restricted rats, which have robustly increased longevity and decreased morbidity as compared with their ad libitum fed counterparts. The second is a methodology that enables us to capture serum components that differ between ad libitum and dietary restricted rats. Direct evidence for the utility of our invention to complete this component is shown in FIGS. 2B, 2C, 4 and 5. The third is based on the observation that the metabolites identified are sufficient to group animals by caloric intake. This is shown in FIG. 5. The fourth component is based on the observation that at least some of the markers (metabolites) identified in non-human species can be identified in humans. This is true because of the overall similarity between the metabolism of all mammals. Direct confirmation has been previously demonstrated by Milbury et al in their comparative studies of the bear and humans {46}. Finally, the fifth component is the ability of these markers, or subsets of them, to predict disease risk or diagnose disease in humans. This follows from the general similarity of metabolism between mammals, the strong association of many human diseases with caloric intake (e.g., some cancers, type II diabetes, cardiovascular and cerebrovascular diseases), and the established efficacy of DR against most forms of morbidity. Furthermore, the method for determining which subsets of markers have utility includes generation and verification of markers in animals coupled with testing these markers in human populations using methods developed for human epidemiology. Intermediate steps, such as testing multiple patterns in humans with defined nutritional intake, may be used to facilitate and strengthen the approach.

FIG. 5 shows the grouping of the sera samples from 6 and 12 month old rats based on the metabolites that were identified as differing between 6-month old AL and DR rats. The dendrograms in FIG. 5 (panels A and B) were generated using the hierarchical cluster analysis package from the Einsight data analysis package. Hierarchical cluster analysis is a method of data analysis that emphasizes the natural groupings of the data set. In contrast to analytical methods that emphasize distinguishing differences between two groups, hierarchical cluster analysis uses algorithms that reduce complex data sets to establish these groups without preconceived divisions. In this dendrogram, relative similarity within the total study population increases as one moves from right (0.0) to left (1.0, biochemical identity) on the horizontal axis. The smaller the distance is from identity (left side) to the point at which two samples (groups) are linked by a vertical line, the greater the relatedness of the two samples (groups). Alternatively, the closer the split between two samples is to the right of the figure, the greater the disparity between two samples or groups of samples.

Additional analyses were also conducted using Eigenvector or principal component analysis (PCA), which determines those analytes that contribute most heavily to the separation of groups (panels C and D of FIG. 5). In this type of analysis, the two PCA components that were most significant at explaining the variation in the database are termed PC 1 and 2, respectively. Relative mathematical values were assigned to the two groups of analytes that best discriminate the data set (PC-1 and PC-2, exact values are arbitrary). A scattergram then was plotted using the PC-1 value for the X axis and the PC-2 value for the Y-axis. In the context of the current invention, principal component (Eigenvector) analysis enabled us to identify which of the multiple compounds that may differ between AL and DR animals were the most useful for classification purposes. This analysis also gives a means of estimating the consequences of removing different analytes from the profiles. This type of analysis permits us readily to determine which analytes contribute the most to our ability to distinguish members of one group from members of another (e.g., humans at high risk for developing a specific disease vs humans not at high risk for developing that disease).

As shown in FIG. 5, data of sufficient power can be generated such that both hierarchical cluster analysis and principal component analysis were able to separate the rat sera by dietary group in both the initial cohort of 6 month old rats (with 100% accuracy, FIG. 5A and 5C) and two independent cohorts of 12 and 18 month rats (with >85% accuracy, FIGS. 5B and SD. The initial group confirms a series of markers that, by themselves, retain a sufficient fraction of the information present in sera to enable one to correctly identify the origin of the samples. More importantly, the studies in the two independent data sets reveal that the data is able to identify a series of markers with sufficient power to correctly identify >85% of unknown, independent samples. Equally successful separation was achieved at all three ages regardless of whether all 22 markers were used or just the 6 markers that differed in both 6 and 12 month samples. Misclassifications were limited to a small subset [2–4 rats] of the cohort, and were dependent on the markers used (6 or 22) and the exact algorithms used to conduct the analysis.

Serum Markers Distinguish AL and DR Rats

Figure 5C:
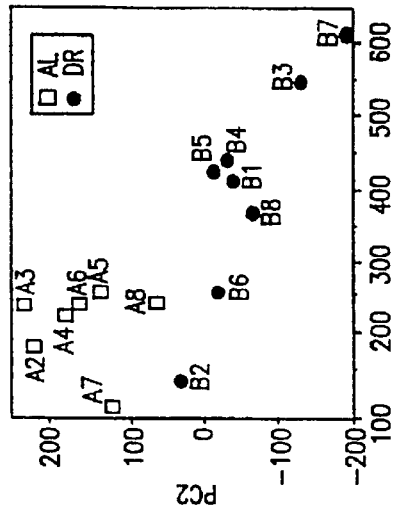
Figure 5D:
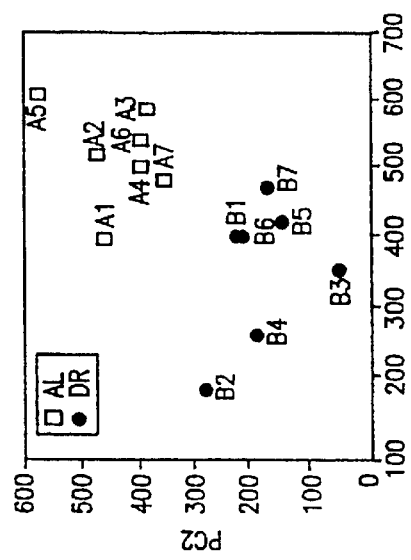

The 22 serum metabolites identified as potential markers in 6 month old AL and DR rats (FIG. 4, left of vertical line) and the 6 markers shown to be replicable in 6 and 12 month old rats (FIG. 4, asterisks) were used to determine groupings of 3 sets of AL and DR rats (6, 12, and 18 months, 18 month data not shown). Rat designations (e.g., A1) are consistent within age groups (vertically, e.g., A1 in FIGS. 5A and 5C are the same rat, but A1 in FIGS. 5A and 5B are not). Both hierarchical cluster analysis (A,B) and principal component (Eigenvector) analysis (C,D) of the data are shown. (A) Dendrogram of analysis of the sera from 14 6 month old rats. All 22 compounds were used to determine the natural groupings, but similar results were also obtained using only the 6 replicable markers. (B) Dendrograrn of analysis of the sera from 15 12 month old rats (independent test set). All 22 compounds were used to determine the natural groupings. Similar results were also obtained using only the 6 replicable markers and in samples from 18 month old rats. (C) Principal component analysis of sera from the 14 6 month old rats using all 22 markers. Similar results were also obtained using only the 6 replicable markers. (D) Principal component analysis of the sera from the 15 12 month old rats in the independent test set using the 6 replicable markers. Similar results were also obtained using all 22 markers as well as in samples from 18 month old rats. All analysis was based on first pass data—meaning that the HPLC data analysis software required no further training and no human intervention to collect data of sufficient quality to distinguish AL and DR rats.

The data presented in FIGS. 2, 4 and 5 demonstrate that the present invention permits identification markers that reproducibly differ between AL and DR rats, and that metabolite profiles based on these markers are sufficiently powerful to assign sera samples into correct dietary groups by hierarchical cluster analysis and principal component analysis with >85% accuracy—even when these phenotypes may be partially obscured by age-related and/or individual variation. Increasing the "N" will readily increase the accuracy and power of these results by generating larger, and thus more informative, training sets, and by increasing the signal-to-noise ratio by removing noninformative metabolites from the profiles. Furthermore, building extended databases using rats maintained on specifically modified feeding regimens will enable one to parse out metabolites and metabolic profiles to increase power (e.g., one can identify markers that reflect a short term diet and distinguish those which reflect a truly long term reduced caloric intake). Both of these sets of markers may have utility for different uses. Finally, the data obtained can be analyzed by univariate, multivariate, or pattern recognition based analyses, and that these analyses may detect utility not seen with other analyses.

It thus appears that HPLC with coulometric-array detectors advantageously may be employed to identify specific chemical markers, i.e. metabolites, sets of metabolites, and/or metabolic profiles (detected in sera or other biological samples, plasma, platelets, saliva, and urine), that separates AL from DR rats or other animals, and that such metabolites, sets of metabolites, or metabolic profiles in turn may be used to diagnose or predict disease states or future risks of diseases. Such diseases may include degenerative diseases such as diabetes, in particular, type II diabetes, cardiovascular disease, stroke, heart attack, cerebrovascular disease, and other diseases whose etiology has been established to or hypothesized to (e.g., Alzheimer's {1}) be modified by diet or nutrition, although utility in other diseases is also considered, including, neoplastic and non-neoplastic diseases, such as breast cancer, colon cancer, pancreatic cancer, lymphoma, prostrate cancer and leukemia, neurological diseases, neurodegenerative diseases, autoimmune diseases, endocrine diseases, renal disease, Huntington's disease, Parkinson's disease, Lou Gehrig's disease, and the like, as well as sensitivity to toxins, e.g. industrial and/or environmental toxins. Moreover, applying the technique of the present invention to a larger number of samples will permit one to observe greater number of chemical pattern characteristics, and to identify new chemical patterns and/or new markers specific to particular diseases and/or subclinical conditions that in the future may develop into a specific disease. In turn, this may permit early intervention and thus possibly head off the development of the disease. The invention also advantageously may be employed for diagnosing other disease conditions, or sub-clinical conditions, i.e. before observable physical manifestations, that in the future may develop into disease conditions. Similarly, in addition to disease, the assessment of nutritive status may be useful as a medical test under a variety of potential clinical settings, or in controlling epidemiological or pharmaceutical testing, although other utilities are contemplated.

REFERENCES

1. Grant, W B, Dietary Links to Alzheimere's Disease, Alzheimer's Disease Review, 2, 42–55, 1997.
2. Kristal, B. S. and B P Yu, Aging and its modulation by caloric restriction, in. B. P. Yu, Ed. Modulation of Aging Processes by Dietary Restriction, CRC Press, 1994. pp. 1–35.
3. Weindruch, R. and R. Walford, The Retardation of Aging and Disease by Dietary Restriction, Charles C. Thomas, St. Louis, 1988.
4. Yu, B. P., Aging and oxidative stress: modulation by dietary restriction, Free Rad. Biol. Med., 21:651–668, 1996.

5. McCay, C. M., Cellulose in the diet of rats and mice, J. Nutr., 435–447, 1935.
6. Maeda, H., C A Gleister, E J Masoro, I Murata, C A McMahan, B P Yu, Nutritional influences on aging of Fisher 344 rats: II Pathology, J. Gerontol., 40:671–688, 1985.
7. Carlson, A J, and F Hoelzel, Apparent prolongation of the life span of rats by intermittent fasting, J. Nutr., 31:363–375, 1946.
8. Goodrick, C. L., D K Ingram, M A Reynolds, J R Freeman, and N. Cider, Effects of intermittent feeding upon body weight and lifespan in inbred mice: Interaction of genotype and age, Mech. Age. Dev., 55:69–87, 1990.
9. Cheney, K E, R K Liu, G S Smith, R E Leung, M R Mickey, and R L Walford, Survival patterns in C57BL/6J mice subjected to undernutrition, Exp. Gerontol., 15:237–258, 1980.
10. Ross, M H, and G. Bras, Food preference and length of life, Science, 190:165–167, 1970.
11. Weindruch, R, R L Walford, Dietary restriction in mice beginning at 1 year of age: Effect on life-span and spontaneous cancer incidence, Science, 215; 1415–1418, 1982.
12. Nolen, G A, Effect of various restricted dietary regimens on the growth, health, and longevity of albino rats, J. Nutr., 102:1477–1494, 1972.
13. Tannenbaum, A., The dependence of tumor formation on the composition of the calorie-restricted diet as well as on the degree of restriction, Cancer Res., 5:616–625, 1945.
14. Iwasaki, K, C A Gleister, E J Masoro, C A McMahan, E-J Seo, and B P Yu, The influence of dietary protein source on longevity and age-related disease processes of Fischer rats, J. Gerontol., 43:B5–B 12, 1988.
15. Iwasaki, K., C A Gicister, E J Masoro, C A McMahan, E-J Seo, B P Yu, Influence of the restriction of individual dietary components on longevity and age-related disease of Fischer Rats: the fat component and the mineral component, J. Gerontol., 43:B13–21, 1988.
16. Stucklikova, E. M. Juricova-Horakova, Z. Deyl, New aspects of the dietary effect of life prolongation in rodents. What is the role of obesity in aging? Exp. Gerontol., 10:141–144, 1975.
17. Lane, M A, D J Baer, W V Rumpler, R Weindruch, D K Ingram, E M Tilmont, R G Cutler, G S Roth, Calorie restriction lowers body temperature in rhesus monkeys, consistent with a postulated anti-aging mechanism in rodents, Proc. Natl. Acad. Sci., 93:4159–64, 1996.
18. Kemnitz, J W, E B Roecker, R Weindruch, D F Elson, S T Baum, R N Bergman, Dietary restriction increases insulin sensitivity and lowers blood glucose in rhesus monkeys, Am. J. Physiol., 266:E540–7, 1994.
19. Hansen, B C, H K Ortmeyer, N L Bodkin, Prevention of obesity in middle-aged monkeys: Food intake during body weight clamp, Obesity Res., 3 Suppl 2:199S–204S, 1995.
20. Bodkin, N L, H K Ortmeyer, B C Hansen, Long-term dietary restriction in older-aged rhesus monkeys: effects on insulin resistance, J. Gerontol., 50:B142–147, 1995.
21. Lane, M A, S S Ball, D K Ingram, R G Cutler, J. Engel, V Read, G S Roth, Diet restriction in rhesus monkeys lowers fasting and glucose-stimulated glucoregulatory end points, Am. J. Physiol., 268:E941–8, 1995.
22. Walford, R L, L Weber, S Panov, Caloric restriction and aging as viewed from Biosphere 2, Receptor, 5:29–33, 1995.
23. Walford, R L, S B Harris, M W Gunion, The calorically restricted low-fat nutrient-dense diet in Biosphere 2 significantly lowers blood glucose, total leukocyte count, cholesterol, and blood pressure in humans, Proc. Natl. Acad. Sci., 89:11533–537, 1992.
24. Berg, B N, and H S Simms, Nutrition and longevity in the rat. II. Longevity and onset of disease with different levels of food intake, J. Nutr., 71:255–263, 1960.
25. McCay, C. M., G Sperling, L L Barnes, Growth, aging, chronic diseases and life span in rats, Arch Biochem. Biophys, 2:469–479, 1943.
26. Fernandes, G P, E J Friend, E J Yunis, R A Good, Influence of DR on immunologic function and renal disease in (NZB x NZW) F1 mice, Proc. Natl. Acad. Sci., 75:1500–1504, 1978.
27. Mark, D A, DR Alonso, F Quimby, H T Thaler, Y T Kim, G Fernandes, R A Good, M E Weksler, Effect of nutrition on disease and life span, I. Immune responses, cardiovascular pathology, and lifespan in MRL mice, Am. J. Pathol., 117:110–124, 1984.
28. Lloyd, T., Food restriction increases life-span of hypertension animals, Life Sci., 34:401–407, 1984.
29. Russell, J C, D G Koeslag, V Manickavel, R M Amy, P J Dolphin, Effects of advancing age and severe food restriction on pathological processes in the insulin resistant JCR:LA-corpulent rat, Diabetes Res., 15:53, 1990.
30. Shimokawa, I, and Y Higami, Effect of dietary restriction on pathological processes, in. B. P. Yu, Ed. Modulation of Aging Processes by Dietary Restriction, CRC Press, 1994. pp. 247–266.
31. Weindruch, R., R J Walford, S Fliegiel, D Guthrie, The retardation of aging in mice by dietary restriction: longevity, cancer, immunity and lifetime energy intake, J. Nutr., 116:641–654, 1986.
32. Fernandes, G., B. Chandrasekar, D A Troyer, J T Venkatraman, R A Good, Dietary lipids and calorie restriction affect mammary tumor incidence and gene expression in mouse mammary tumor virus/v-Ha-ras transgenic mice, Proc. Nat. Acad. Sci., 92:6494–6498, 1995.
33. Kritchevsky, D., M M Weber, D M Klurfeld, Dietary fat versus caloric content in initiation and promotion of 7,12-dimethylbenz(a)anthracene-induced mammary tumorigenesis in rats, Cancer Res., 44:3174–3177, 1984.
34. Klurfeld, D M, M M Weber, D Kritchevsky, Inhibition of chemically induced mammary and colon tumor promotion by caloric restriction in rats fed increased dietary fat, Cancer Res., 47:2759–2762, 1987.
35. Sinha, D K, R L Gebhard, J E Pazik, Inhibition of mammary carcinogenesis in rats by dietary restriction, Cancer Lett., 40:133–141, 1988.
36. Tucker, M J, The effect of long-term food restriction on tumours in rodents, Int. J. Cancer, 23:803–807, 1987.
37. Yu, B P, Food restriction research: past and present status, Rev. Biol. Res in Aging, 4:349–371, 1990.
38. Sabatino, F, E J Masoro, C A McMahan, R W Kuhn, Assessment of the role of the glucocorticoid system in aging processes and in the action of food restriction, J. Gerontol., 46:B 171–179, 1991.
39. Holehan, A M, B J Merry, The control of puberty in the dietary restricted female rat, Mech. Age. Dev., 32:179–191.
40. Green, G, D Guan, J Morisset, A Spannagel, E Paul, Preservation of exocrine pancreatic function in food-restricted rats, Pancreas, 8:757, 1993.
41. Herlihy, J T, C. Stacy, H A Bertrand, Long term food restriction depresses serum thyroid hormone concentrations in the rat, Mech. Age. Dev., 53:9, 1990.
42. Masoro, E J, R J M McCarter, M S Katz, C A MacMahan, Dietary restriction alters characteristics of glucose fuel use, J. Gerontol., 47:B202–208, 1992.

43. Taylor, A, R D Lipman, J Jahngen-Hodge, V Palmer, D Smith, N Padhye, G E Dallal, D E Cyr, E. Laxman, D Shepard, Dietary calorie restriction in the Emory mouse: effects on lifespan, eye lens cataract prevalence and progression, levels of ascorbate, glutathione, glucose, and glycohemoglobin, tail collagen breaktime, DNA and RNA oxidation, skin integrity, fecundity, and cancer, Mech. Age. Dev., 79:33–57, 1995.

44. Taylor, A., J Jahngen-Hodge, D E Smith, V J Palmer G E Dallal, R D Lipman, N Padhye, B Frei, Dietary restriction delays cataract and reduces ascorbate levels in Emory mice, Exp. Eye Res., 61:55–62, 1995.

45. Harris, S B, M W Gunion, M J Rosenthal, R L Walford, Serum glucose, glucose tolerance, corticosterone and free fatty acids during aging in energy restricted mice, Mech. Age. Dev., 73:209–21, 1994.

46. The Tenth International Conference on Bear Research and Management of Jul. 16–20, 1995 at Fairbanks, Ak.

What is claimed is:

1. A method for diagnosing and/or predicting disorders comprising the steps of analyzing biological samples of ad libitum-fed individuals and of dietary-restricted individuals; wherein said biological samples comprise electrochemically responsive compounds; and said samples are passed first through a liquid chromatographic column for achieving time-space separation of materials eluting from the column, and the separated materials are then passed through an electrochemical detection apparatus whereby to generate electrochemical patterns of said electrochemically responsive compounds to quantify molecular constituents in said sample and generate frequency distribution patterns representative of molecular constituents of said samples; comparing said frequency distribution patterns of said samples of ad libitum-fed and dietary-restricted individuals to (1) identify differences and frequency distribution patterns, and (2) create a data base of patterns of markers that distinguish ad libitum-fed and dietary-restricted individuals, and screening a biological sample from an individual for patterns of electrochemically responsive compounds replicating said markers whereby to diagnose or predict relative risk for the development of a disorder of said individual.

2. A method according to claim 1, wherein said samples comprise body fluids.

3. A method according to claim 2, wherein said body fluids are selected from the group consisting of serum, plasma, platelets, saliva and urine.

4. A method according to claim 1, wherein said disorder is selected from the group consisting of neoplastic or non-neoplastic disease, cardiovascular or cerebrovascular disease, renal disease, autoimmune disease, neurological or neurogenerative disease, endocrine disease, and diabetes.

5. A method according to claim 1, wherein said disorder is selected from the group consisting of breast cancer, colon cancer, pancreatic cancer, lymphoma, prostate cancer and leukemia.

6. A method according to claim 1, wherein said disorder comprises glomerulonephritis.

7. A method according to claim 1, wherein said disorder comprises periarateris.

8. A method according to claim 1, wherein said disorder is selected from the group consisting of myocardial degeneration, heart disease and stroke.

9. A method according to claim 1, wherein said disorder comprises altherosclorosis.

10. A method according to claim 1, wherein said disorder comprises pituitary adnoma.

11. A method according to claim 1, wherein said disorder comprises type II diabetes.

12. A method according to claim 1, wherein said disorder comprises sensitivity to toxins.

13. A method according to claim 1, wherein said comparison is conducted using univariat statistics.

14. A method according to claim 1, wherein said comparison is conducted using multivariat statistics.

15. A method according to claim 1, wherein said comparison is conducted using hierarchical cluster analysis.

16. A method according to claim 1, wherein said comparison is conducted using principal component analysis.

17. A method according to claim 1, wherein said comparison is conducted using pattern recognition algorithms to qualitatively and quantitatively identify metabolic profiles and relationships of said molecular constituents.

18. A method according to claim 1, including the step of further separating said electrochemically responsive compounds by electrochemical response characteristics in said electrochemical detection apparatus.

* * * * *